US006577890B1

United States Patent
Hayes et al.

(10) Patent No.: US 6,577,890 B1
(45) Date of Patent: Jun. 10, 2003

(54) METHODOLOGY TO OPTIMIZE POSITIONING OF MULTI-DETECTOR GAMMA CAMERAS UTILIZING TANGENTIAL DETECTOR MOTION

(75) Inventors: John M. Hayes, Macedonia, OH (US); Piotr J. Maniawski, Sagamore Hills, OH (US); Stephen Miller, Knoxville, TN (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 257 days.

(21) Appl. No.: 09/659,436

(22) Filed: Sep. 8, 2000

(51) Int. Cl.[7] .................................................. A61B 6/00
(52) U.S. Cl. .............. 600/436; 250/363.04; 250/363.05
(58) Field of Search ................................. 600/436, 407, 600/409; 250/363.05, 363.04, 363.08; 378/209

(56) References Cited

U.S. PATENT DOCUMENTS

| | | | | |
|---|---|---|---|---|
| 5,559,335 A | * | 9/1996 | Zeng et al. ............ | 250/363.04 |
| 5,838,009 A | * | 11/1998 | Plummer et al. ...... | 250/363.05 |
| 6,137,109 A | * | 10/2000 | Hayes ................... | 250/363.05 |

OTHER PUBLICATIONS

Picker—AXIS and IRIX Accessories brochure, 1999.
Picker—Beacon–Non–Uniform Attenuation Correction brochure, 1999.
Picker—AXIS VT Technology, Transforming Technology into Knowledge brochure, 1999.

* cited by examiner

Primary Examiner—Quang T. Van
(74) Attorney, Agent, or Firm—Fay, Sharpe, Fagan, Minnich & McKee, LLP

(57) ABSTRACT

A nuclear medicine imaging device includes a plurality of detector heads (10) mounted to a movable gantry for rotation around an examination region (12). The detector heads (10) include a housing (28) which surrounds a radiation sensitive crystal (26) which converts received radiation events. A positioning mechanism on the gantry maintains a relationship between the detector heads (10) such that the housing for one detector head lies adjacent to and overlaps the housing for another detector head. During an imaging event, the gantry rotates the detector heads (10) about a region of interest (12) while radiation events are sampled. At a predetermined position relative to the area of interest, the overlapping of the detector heads is reversed.

15 Claims, 2 Drawing Sheets

METHODOLOGY TO OPTIMIZE POSITIONING OF MULTI-DETECTOR GAMMA CAMERAS UTILIZING TANGENTIAL DETECTOR MOTION

BACKGROUND OF THE INVENTION

The present invention relates to the art of nuclear medicine and diagnostic imaging. It finds particular application in conjunction with 3D single photon emission computed tomography (SPECT), and will be described with particular reference thereto. It is to be appreciated that the present invention is amenable to other diagnostic modes and other like applications.

Diagnostic nuclear imaging is used to study a radio nuclide distribution in a subject. Typically, one or more radiopharmaceutical or radioisotopes are injected into a subject. The radiopharmaceutical are commonly injected into the subject's bloodstream for imaging the circulatory system or for imaging specific organs which absorb the injected radiopharmaceutical. A gamma or scintillation camera detector head is placed near to a surface of the subject to monitor and record emitted radiation. Often, the detector head is rotated or indexed around the subject to monitor the emitted radiation from a plurality of directions. This data is reconstructed into a three-dimensional image representative of the radiopharmaceutical distribution within the subject.

Each detector head typically includes an array of photo multiplier tubes facing a large scintillation crystal. Each received radiation event generates a corresponding flash of light or scintillation that is detected by the photo multiplier tubes (PMT). Each photo multiplier tube that detects an event produces a pulse, pulses from tubes closest to the flash being bigger than pulses from further away tubes. The pulses from the individual PMT's are combined to generate x and y spatial coordinates approximating the location of the scintillation event in the coordinate system of the crystal. Ambiguities arise as the distance between the tube and the subject increase. Long bore collimators mounted to the incident face of the camera are a known method to reduce these ambiguities.

Initially for SPECT, a single detector was mounted on a gantry to rotate about a subject. The orbit could consist of either 180 or 360 degrees of detector rotation. The application would dictate the necessary coverage angle. In the case of non-attenuation corrected SPECT imaging of the heart, it may be advantageous to perform 180 degree studies beginning at 45 degrees (assuming that 0 is below the table, counter clockwise rotation, and the subject is situated head first within the gantry). This and similar functioning 180 degree scans for other applications have been named the "best 180" since the emission photons experience the least attenuation along with the least amount of collimator blurring.

The fundamental problem with SPECT distance blurring resides with the physics of collimating gamma photons. Collimating consists of placing a regularly spaced grids covering the detector field of view to limit receipt of photons to perpendicular or other fixed preselected rays. Two primary features of the collimator characterize the effects on photon event acceptance: collimator hole diameter and hole length. This hole-length combination defines a solid cone of acceptance for which any photon within this cone could potentially be counted. The larger the diameter of the cone at a specified distance, the greater the variance in incident ray angles and the poorer the spatial resolution of the resulting reconstructed image. As the cone diameter increases for a given distance, the more ambiguous the point of origin of the scintillation becomes.

When the best 180 is performed with a single detector, scan times are typically 40 minutes or more. To reduce total scan time, a second detector can be added positioned at 90 degrees to form an "L". In this case, 180 degrees of data can be acquired in 90 degrees of gantry rotation, which cut the scan time in half. Given that the photon emission rates are adequate, this virtually allows the study rate to double. However, gamma camera detectors are surrounded by thick, lead shielded walls and have a useful field of view (UFOV) which is significantly narrower than the total detector width. In this case, dual detector "L" shaped detector configurations suffer the effect of placing one or both detectors at a sub-optimum distance from the patient. These dual "L" detectors have typically been configured in a fixed 90 degree orientation. This approach is not necessarily optimal with regards to performing the best 180. It suffers from physical limitations due to detector design which restricts the "reach" or the distance from the detector physical edge to the useful field of view (UFOV) edge to typically 3.5–9.0 cm. That is, there is a 3.5–9 cm dead space in front of each detector head that can be received by only one detector. To avoid subject field of view truncation on the detector, subjects are typically positioned at the reach distance from both detectors. Undesirably, this position places the incident faces of both cameras 3.5–9 cm further from the subject than the optimal distance. Also in certain portions of the orbit, one of the detectors swings away from the subject. These two factors create extra distance between the detector and the subject which results in blurring even with collimation.

Some attempts have been made to reduce the distance between incident faces of cameras and the subject and resulting blurring such as cutting off corners to allow the detectors to fit closer together. Unfortunately, this reduces the shielding to the detector components while still not eliminating the gap between the two UFOV's. Others have used long bore collimators to "connect" the corners. Although this does reduce collimator blur, it dramatically reduces the detector sensitivity in an already count starved study type. Others have moved the table to keep the subject as close to the detector as possible. Unfortunately, this adds considerable complexity to manufacture (table robotics), and also places a high burden on preprocessing raw data to maintain a constant center of rotation. It further does not optimize the subject-detector distance in the region of interest since the detector edge to UFOV reach problem is still present. Moving the table during acquisition may also be disconcerting to some patients. Others have tried developing image processing and reconstruction techniques to reduce the blur inherent in collimated imaging. Some of these techniques produce unwanted reconstructed image artifacts or increased noise.

Most common cardiac studies performed today with the "L" shaped detector configuration incorporating a moving table to keep the patient in the UFOV. As previously stated, while this configuration only requires 90 degrees of detector rotation, it does not provide a minimum subject to detector distance as the detectors orbit the subject. Resulting blurred projection data causes a loss in reconstructed spatial resolution for which reliance upon post acquisition restoration techniques is placed.

The present invention contemplates a new and improved method and apparatus which overcomes the above-referenced problems and others.

SUMMARY OF THE INVENTION

In accordance with one embodiment of the present invention, a nuclear camera system includes a plurality of detector heads mounted around an examination region. A processor reconstructs signals from the detector heads into an image representation. Each detector head includes a housing which surrounds and shields a radiation sensitive incident face. A positioning mechanism is also included which selectively moves the detector heads with respect to the examination region to establish a relationship between the detector heads such that the housing for one head lies adjacent to and overlaps the housing for another detector head.

In accordance with another aspect of the present invention, the relationship between the detector heads changes or reverses at a selected point during a scan.

In accordance with another embodiment of the present invention, a method includes placing a first radiation detector housing adjacent to a second radiation detector housing with the incident faces of the radiation detectors toward the area of interest. The housing of one of the detectors overlaps the housing of the other detector. The method further includes rotating the detectors about a selected portion of the area of interest, and adjusting a position of the radiation detectors.

In accordance with another aspect of the present invention, the adjusting step includes reversing the overlap of the radiation detectors.

In accordance with another embodiment of the present invention, a method of diagnostic imaging includes placing an object of interest into an examination region observable to a plurality of detector heads and injecting a radioisotope into the object. A first detector head is then radially moved relative to the object of interest to minimize a distance between an incident face of the first detector head and the object of interest. A second detector head is tangentially moved to overlap the housing of the first detector head. The detector heads are then rotated partially about the examination region while receiving radiation events.

One advantage of the present invention resides in improved spatial resolution of reconstructed images.

Another advantage of the present invention resides in decreased reliance on post image acquisition processing techniques to reduce distance dependent blurring.

Another advantage resides in efficient data acquisition times.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating the preferred embodiments and are not be construed as limiting the invention.

DETAILED DESCRIPTION OF THE PREFERRED EMBODIMENTS

Figure 1:
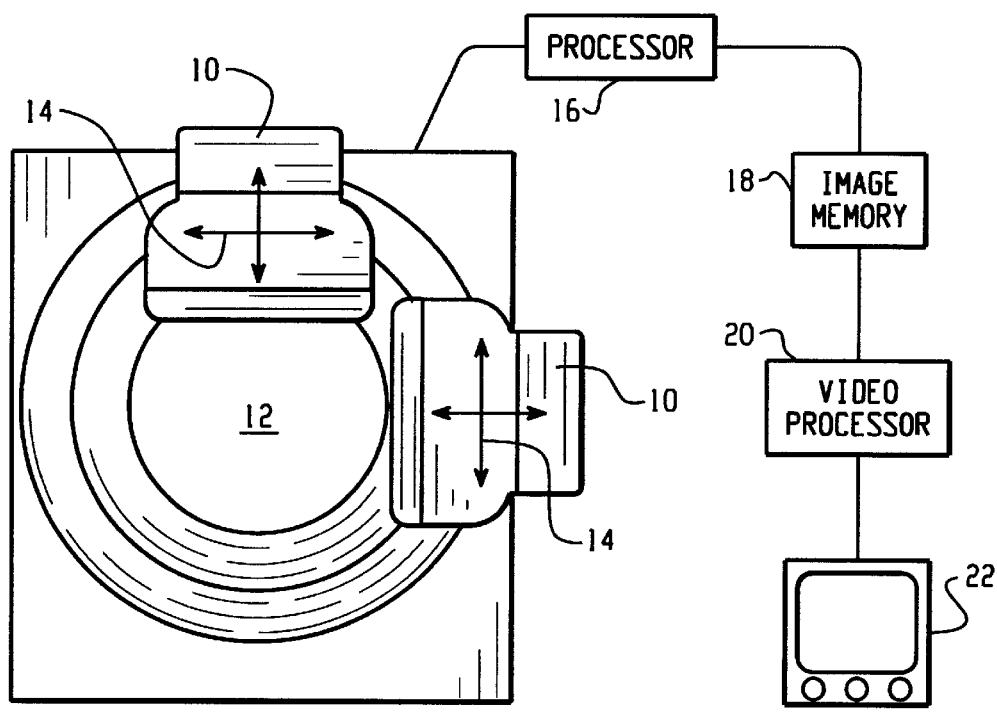
FIG. 1 is a diagrammatic illustration of a nuclear medicine imaging device in accordance with an embodiment of the present invention.

With reference to FIG. 1, a nuclear medicine imaging machine includes a number of detector heads 10 circumferentially about a region of interest 12. Typically, a subject from which images are desired is injected with one or more radiopharmaceutical or radioisotopes and placed in the region of interest 12. The presence of these pharmaceuticals within the subject produces emission radiation from the subject, a certain amount of which is detected by the detector heads 10. The detectors are positionable radially, tangentially, and preferably circumferentially to optimize data acquisition as indicated by range of motion arrows 14. That is, mechanical drives (not shown) move each head linearly in and out in a radial direction and linearly side-to-side in a tangential direction. Drive mechanisms for positioning detector heads are taught generally by U.S. Pat. No. 5,717,212 issued Feb. 10, 1998 to Fulton, et al., U.S. Pat. No. 5,569,924 issued Oct. 29, 1996 to Plummer, and U.S. Pat. No. 5,093,575 issued Mar. 3, 1992 to Perusek. Preferably the mechanical drive moves one of the heads circumferentially to change the angle between the heads. The heads are angularly indexed or rotated to collect emission data from a plurality of directions. A processor 16 receives scintillation events and head orientation data from the gantry and processes the information into a volumetric image representation defined by radiation received by each detector at each coordinate. The image representation is then stored in an image memory 18 for manipulation by a video processor 20 and display on an imaging display 22.

Figure 2:
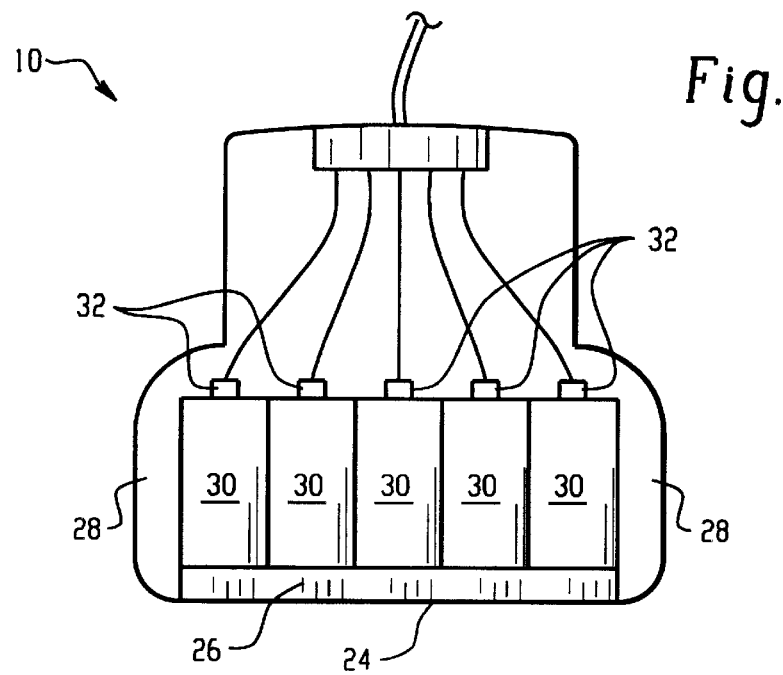
FIG. 2 is an enlarged view of one of the detector heads of FIG. 1, cut away to partially review the internal elements.

Referring now to FIG. 2, each camera has a radiation sensitive receiving face 24 facing the area of interest 12. The receiving face 24 typically includes a scintillation crystal, such as a large doped sodium iodide crystal 26, that emits a flash or scintillation of light or photons in response to incident radiation. A lead housing 28 surrounds and shields the scintillation crystal 26 from stray radiation. An array of photo multiplier tubes 30 receive the light and convert it into electrical signals. An analog-to-digital converter 32 is associated with the output of each photo multiplier tube 30 for converting its analog, electrical output signal into a series of digital values. The digital outputs of the converters 32 following each scintillation event are processed and corrected to generate an output signal indicative of (1) a position coordinate on the detector head at which each radiation event is received, and (2) an energy value of each event. The energy is used to differentiate between various types of radiation and to eliminate noise and scattered radiation.

Referring now to FIGS. 3A–3D, an exemplary rotation about an examination area is illustrated. In the example of FIG. 3, a cardiac set-up is illustrated with a cross section of a subject 40 loaded supine onto a gantry (not shown). The cardiac region 42 is the primary area of interest. As a point of reference throughout FIGS. 3A–3D for subsequent rotation, zero degrees is arbitrarily selected straight down under the table or at the bottom of the figure, i.e. at 6 o'clock. Angles are indexed counter clockwise. Accordingly, detector $10_1$ is located at 45 degrees and detector $10_2$ is located at 135 degrees. Gantry orbit direction is counter clockwise. At the starting point of the scan in FIG. 3A, the detector $10_2$ is illustrated as being moved radially inward to the minimum clearance for optimal resolution. Detector 10 is moved radially outward and translated tangentially as necessary to overlap detector $10_2$ by the width of the housing. The detector $10_2$ is preferably shifted tangentially to bring the detector $10_1$ closer to the subject. Optimally, the edge of the UFOV of detector $10_2$ is tangential to an edge of the subject and the edge of the UFOV of the detector $10_1$ is coincident with a front surface of the collimators of the detector $10_2$.

Figure 3A:
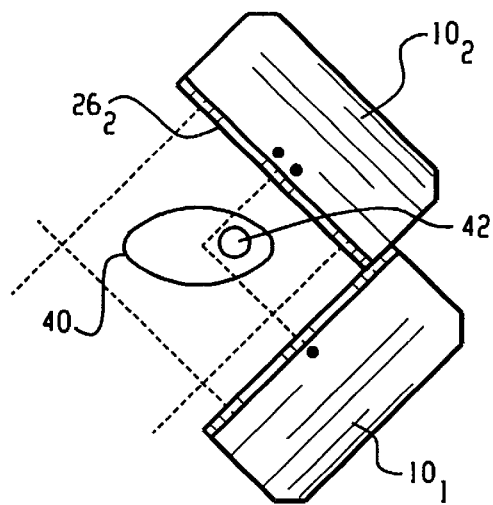
FIGS. 3A–3D are successive illustrations of a subject within an examination region at selected times during an examination employing an embodiment of the present invention.
Figure 3B:
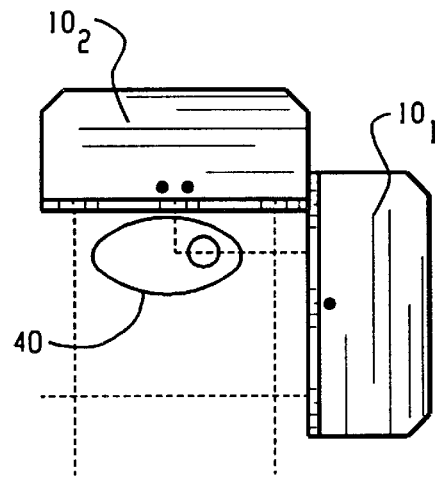

Referring now to FIG. 3B, the detectors 10 have rotated just under 45 degrees from their starting points and have maintained the same detector overlap configuration up to this point. The detector $10_2$ has translated, if necessary, to keep the subject 40 within the UFOV while optimizing the approach of detector $10_1$ to the subject. As is apparent by reference to FIG. 3B, detector $10_2$ maintains not only the overlap of part of detector $10_2$'S housing but also maintains a close physical proximity to the subject 40.

Figure 3C:
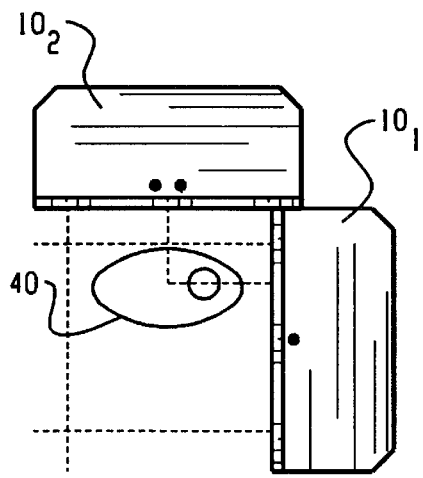

Referring now to FIG. 3C, the detectors 10 have completed 45 degrees of rotation, so that detector $10_1$ is at 90 degrees while detector $10_2$ is at 180 degrees. At this point during the scan, the positioning drives have reversed the detector overlap configuration so that detector $10_1$ now overlaps slightly detector $10_2$ which accordingly places detector $10_1$ closer to the subject 40.

Figure 3D:
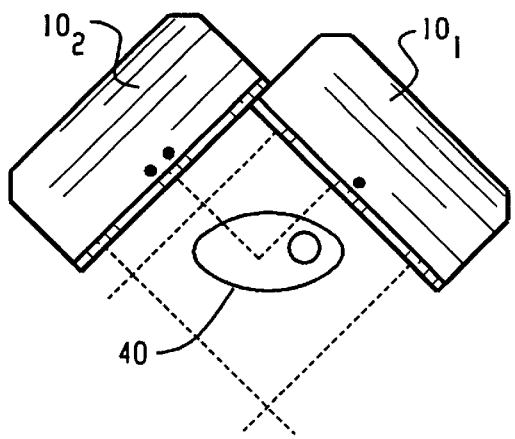

Referring now to FIG. 3D, at the completion of the scan, detector $10_2$ is at 225 degrees while detector $10_1$ is at 135 degrees. Note that the overlap configuration has been maintained since the reversal illustrated in FIG. 3C.

It is now apparent that by overlapping the detectors, it is possible to circumvent the gap between the UFOV (indicated by dashed lines) and the detector edge on one detector for a 180 degree acquisition. The overlap allows one of the two detectors to be as close as possible to the subject. During orbit rotation, the overlap configuration can be reversed so that the second detector has its turn at being close to the subject. Strategically locating this crossover point allows one to acquire a "Best 90" degree view in a 180 degree study for an organ of interest. This dramatically reduces the reconstructed spatial resolution loss. In addition, this configuration lends itself to maintaining an untruncated field of view which is also necessary to not introduce reconstruction artifacts.

With further reference to FIGS. 3A–3D, the benefits of reconfiguring the detector relative positions during the study can be appreciated. In general, the detectors 10 are positioned such that one overlaps the other up to, but not intruding into, the UFOV. An analogy would be the overlapping pieces of a photo camera shutter iris used to alter the aperture diameter. Such an overlap is performed in two fundamental orientations. For one portion of the orbit, the detector closest to the organ of interest is positioned as close as possible to the subject, while the other detector is farther away from the subject. Then as the detectors rotate, the initial detector moves away from the organ of interest as the second detector moves closer. Realizing this, the overlap configuration is reversed to allow the second detector to be as close as possible to the organ of interest. This "Best 90" degrees of a 180 degree cardiac study will optimize the spatial resolution of the reconstructed image without relying heavily on image processing techniques to reduce for collimator distance dependent blurring.

Note that cardiac detector overlap reversal may not always be optimally at 135 degrees. Typical cardiac imaging protocols require performing one study when the heart is at rest and a second when the heart is under exertion. This may change the orientation of the heart such that an alternate overlap switch-over point may be necessary to maintain optimal patient proximity.

This methodology exploits anatomical asymmetry to increase effectiveness. For example, a person's heart is located more to one side (left) and more to the front (chest). Realizing this, it behooves a data acquisition methodology to incorporate an optimum sampling strategy. The variables to optimize include; distance from the organ of interest, collimator type, and collimator sensitivity. In SPECT imaging, being as close to the subject as possible always improves the image quality. Collimator selection trades off spatial resolution versus sensitivity (count rate). Placing the detector closer to the organ of interest gives more freedom in selecting the appropriate collimator to maintain good image quality.

Typical applications are for cardiac imaging where the heart is nominally placed at 135 degrees (with zero degrees directly under the table and ahead first patient loading into the gantry) and collects 180 degrees of projection data. With two detectors configured in the shape of an "L", the detectors rotate a total of 90 degrees. In this case, the study commences with the first detector placed at 45 degrees and the second at 135 as shown in FIG. 3A. The detector overlap allows the second detector to be the closest to the patient and this configuration is maintained up to 90 degrees as shown in FIG. 3B. After the scan progresses 45 degrees (to 90 degrees for the first detector), the overlap reverses so that the first detector is now the closest to the patient for the final 45 degrees of rotation in the study as illustrated in FIG. 3C. The reversed detector overlap is maintained for the duration of the scan as indicated in FIG. 3D. With this reconfiguration of the detector overlap, the distance to the heart from the detector has been minimized which approximately maintains the spatial resolution of a single detector in as close as possible for the entire 180 degrees of the study.

By utilizing tangential motion coupled with alternating detector surface/edge overlap, the percent change in distance between the detector and imaging object compared to the prior art for 90 degree L configurations is minimized. A fixed distance offset translates into a larger percent distance change for shorter distances than for longer distances. In order to avoid partial data artifacts, the subject 40 is maintained fully within the UFOV of both cameras, through the scan.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A nuclear camera including a plurality of detector heads mounted around an examination region and a processor for reconstructing signals from the detector heads into an image representation, each detector head comprising:

a radiation sensitive electronic assembly defining an outer periphery, the radiation sensitive assembly converting received radiation events into location signals;

a housing surroundingly disposed about the periphery of the radiation sensitive assembly; and a positioning mechanism tangentially adjustable with respect to the examination region which selectively moves the detector heads to establish a relationship between the detector heads such that the housing for a first detector head lies adjacent to and overlaps the housing for a second detector head and reverses the relationship between the detector heads such that the second detector head overlaps the first detector head.

2. The nuclear camera as set forth in claim 1, where the relationship between the detector heads is orthogonal.

3. The nuclear camera as set forth in claim 1, where the relationship between the detector heads includes having a first detector head incident face closely positioned relative to a subject in the examination region and a second detector head incident face offset by at least a distance corresponding to the housing of the first detector head.

4. The nuclear camera as set forth in claim 1, where the relationship between the detector heads changes at selected times during a scan.

5. A method comprising:
placing a first radiation detector adjacent to a second radiation detector, with the incident face of the first radiation detector and the incident face of the second radiation detector toward the area of interest;
overlapping one of the detectors with an other of the detectors;
rotating the radiation detectors about a selected portion of the area of interest; and
reversing the overlap of the radiation detectors.

6. The method as set forth in claim 5, further comprising:
positioning the detectors perpendicular to one another.

7. The method as set forth in claim 6 wherein the detectors are rotated 90° about the area of interest.

8. The method as set forth in claim 5 further including:
injecting a radioisotope into the area of interest;
detecting radiation events in the area of interest that are received through the incident faces of the detectors.

9. The method as set forth in claim 8 further including:
reconstructing a three dimensional diagnostic image representation from the received radiation events.

10. A method of diagnostic imaging including:
placing an object of interest into an examination region observable to a plurality of detector heads;
injecting the object with a radioisotope;
radially moving at least a first detector head relative to the object of interest to minimize a distance between an incident face of the first detector head and the object of interest;
tangentially moving a second detector head such that a housing of the second detector overlaps a housing of the first detector head;
rotating the detector heads partially about the examination region;
receiving radiation events with the detector heads;
reversing the overlap of the detector heads at a selected point during the rotating step;
continuing to receive radiation events with the detector heads; and,
reconstructing an image representation from the received radiation events.

11. The method of imaging as set forth in claim 10, further including:
positioning the detector heads in a perpendicular relationship.

12. The method of imaging set forth in claim 10, wherein each detector head has a usable field of view within which radiation is received and in the tangential moving step:
the second head is tangentially moved until an edge of its usable field of view is adjacent a front face of the first detector head.

13. The method of imaging as set forth in claim 12 wherein during the rotating step:
the first and second detector heads are moved tangentially and radially such that (1) the object is maintained within the usable field of view of the first and second detector heads and (2) the distance between the detector heads and the object are minimized.

14. The method of imaging as set forth in claim 12 wherein in the rotating step:
the detector heads rotate 90°.

15. A method of imaging including:
radially moving at least a first detector head relative to an object of interest in an examination region to minimize a distance between an incident face of the first detector head and the object of interest;
tangentially moving the second detector head such that a housing of the second detector head overlaps a housing of the first detector head;
rotating the detector heads partially about the examination region;
after 45° of rotation, reversing the overlap of the detector heads;
receiving radiation from the object of interest with the detector heads; and
reconstructing an image representation from the received radiation.

* * * * *